United States Patent [19]

Rydell

[11] Patent Number: 5,047,026
[45] Date of Patent: Sep. 10, 1991

[54] ELECTROSURGICAL IMPLEMENT FOR TUNNELING THROUGH TISSUE

[75] Inventor: Mark A. Rydell, Golden Valley, Minn.

[73] Assignee: Everest Medical Corporation, Minneapolis, Minn.

[21] Appl. No.: 546,871

[22] Filed: Jul. 2, 1990

Related U.S. Application Data

[63] Continuation of Ser. No. 414,449, Sep. 29, 1989, abandoned.

[51] Int. Cl.5 ............................................. A61B 17/36
[52] U.S. Cl. .................................... 606/48; 606/39;
128/784; 604/282
[58] Field of Search ................... 128/772, 784-786;
604/281, 282; 606/27, 29, 37, 39, 40, 45-50

[56] References Cited

U.S. PATENT DOCUMENTS

| | | | |
|---|---|---|---|
| 1,932,258 | 10/1933 | Wappier | 606/49 |
| 4,311,143 | 1/1982 | Komiya | 606/47 |
| 4,674,498 | 6/1987 | Stasz . | |
| 4,802,476 | 2/1989 | Noerenberg et al. . | |
| 4,869,248 | 9/1989 | Narula | 128/786 |
| 4,905,691 | 3/1990 | Rydell . | |
| 4,920,980 | 5/1990 | Jackowski | 604/95 |
| 4,976,711 | 12/1990 | Parins et al. | 606/78 |

FOREIGN PATENT DOCUMENTS 2501034  9/1982  France .............................. 600/50

Primary Examiner—Stephen C. Pellegrino
Assistant Examiner—Robin R. Longo
Attorney, Agent, or Firm—Haugen and Nikolai

[57] ABSTRACT

An electrosurgical implement for tunneling through tissue for effecting drainage of an organ or to restore patency to a blood vessel is described. The implement comprises a stainless steel, helically wound, wire body similar to a conventional guidewire of the type used in angiography, angioplasty or in implanting cardiac pacing leads. The exterior of the guidewire is coated with an insulating material, save for one or two convolutions at its distal end. A core wire having a Teflon ® shrink tube surrounding it over substantially its entire length is disposed within the lumen of the helical guidewire and only a short segment of the distal end of the core wire is allowed to extend out from the distal end of the guidewire. This short segment is stripped free of insulation. The implement may be routed through an endoscope into the stomach or colon and when an RF voltage of an appropriate amplitude is connected across terminals electrically joined to the proximal ends of both of the guidewire and the core wire, an arc discharge is created when the distal end of the implement is brought into contact with tissue, thereby allowing the device to readily pierce this tissue. The same implement may also be used for restoring patency to a blocked blood vessel.

8 Claims, 1 Drawing Sheet

ELECTROSURGICAL IMPLEMENT FOR TUNNELING THROUGH TISSUE

This is a continuation of copending application Ser. No. 07/414,449 filed on Sept. 29, 1989, abandoned.

BACKGROUND OF THE INVENTION

I. Field of the Invention

This invention relates generally to electrosurgical apparatus, and more particularly to an implement dimensioned so that it can be readily made to pass through the vascular system or an endoscope for facilitating the tunneling of the implement through a tissue body.

II. Discussion of the Prior Art

A variety of electrosurgical instruments are presently known and, for the most part, comprise a hand-held scalpel whose blade carries electrodes. The scalpel is adapted to be connected to a RF electrosurgical generator and when appropriately energized, the implement may be used for cutting tissue or coagulating blood. Typical of such a device is the apparatus shown in the Stasz U.S. Pat. No. 4,674,498 and Noerenberg et al U.S. Pat. No. 4,802,476.

Another electrosurgical implement has been designed to facilitate the removal of polyps from the inner wall of the intestine and it generally comprises a wire snare which is arranged to function as a first electrode, the wire also cooperating with an electrode mounted on the distal end of a flexible tubular member surrounding the wire. As the polyp is brought into contact with the both the snare and the conductive tip on the tube, an electric arc is created for severing the neck of the polyp while simultaneously cauterizing the site of the removal. An arrangement of this type is disclosed in the Rydell et al patent application Ser. No. 07/344,073, filed Apr. 17, 1988, now U.S. Pat. No. 4,905,691 and assigned to applicant's assignee.

Still various other electrosurgical implements have been devised for effecting single-purpose electrosurgical procedures. Until the present invention, a need has existed for an elongated, small diameter, flexible, atraumatic device which can be routed through a body channel to the site where cell tissue is to be pierced. For example, such a device may be used to drain a cyst or tumor located within the abdomen by routing the implement through an endoscope into the stomach or colon and from there, tunneling through the wall of the stomach or colon into the neighboring cyst whereby fluid can be readily drained from it.

In carrying out transluminal angioplasty, a need exists for a device which can be used to tunnel through atheromas to restore patency to more distal blood vessels.

SUMMARY OF THE INVENTION

The above-described need is fulfilled in accordance with the present invention by providing a somewhat conventional helically wound, metal guidewire of the type commonly used in routing a catheter or pacing lead through the vascular system to a predetermined site within the body. The exterior surface of the helically wound guidewire is coated with a suitable insulative material, such as a sprayed-on Teflon ®. Anywhere from the most distal one or two convolutions to about ¼" of the helically wound guidewire are stripped free of insulation and thereby comprise a first electrode.

A second electrode is formed by routing a core wire surrounded by an insulating sheath through the lumen of the guidewire so that only a small, uninsulated distal end portion of the core wire is flush with or extends slightly beyond the uninsulated distal convolutions of the guidewire.

When a RF power generator is connected across proximal terminals connected to the core wire and to the conductive guidewire, when the distal end of the implement is brought into contact with tissue, a RF arc is created between the exposed portion of the core wire and the surrounding distalmost turns of the guidewire. The RF arc allows the guidewire to be pushed through tissue deposits which it contacts and, hence, can be used to carry out the procedures mentioned above.

DESCRIPTION OF THE DRAWING

The foregoing features, objects and advantages of the invention will become apparent to those skilled in the art from the following detailed description of a preferred embodiment, especially when considered in conjunction with the accompanying drawing in which.

DESCRIPTION OF THE PREFERRED EMBODIMENT

Figure 1:
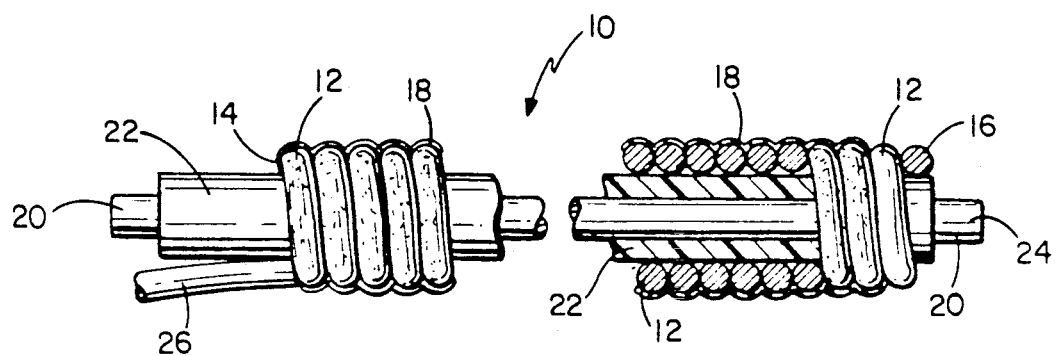
FIG. 1 depicts a partially cross-sectioned, foreshortened side elevation of the implement of the present invention.

Referring to the drawing, there is indicated generally by numeral 10 the electrosurgical tunneling implement in accordance with the present invention. It is seen to include an elongated flexible helically wound wire 12, preferably but not necessarily, formed from stainless steel and having a proximal end 14 and a distal end 16. The helically wound wire may be of differing lengths, depending upon the end-use intended for the implement. Where it is to be used in tunneling through fatty or calcified deposits in a coronary artery, the implement may have an overall length of 120 cms. or more. Where the implement is to be passed through an endoscope into the stomach or into the colon, or if it is used intraoperatively, the overall length of the implement may be somewhat less.

The outside diameter of the helically wound wire 12 is also determined by the intended end-use for the implement and may typically run between 0.014 inches to 0.038 inches. The helically wound wire 12 thus corresponds quite closely to the style of guidewire presently used in coronary angiography and angioplasty procedures.

Sprayed or otherwise deposited on the exterior surface of the helically wound wire 12 is a coating of insulating material 18. The coating should be continuous and be approximately 2 mils thick. Teflon ® material is found to be quite suitable due to its high dielectric strength and lubricity. If the helically wound wire is formed from aluminum, its surface may be rendered electrically insulative by anodizing same.

Fitted within the lumen of the helically wound wire 12 is a conductive core wire 20 which remains insulated from the helically wound wire 18 by a plastic sheath 22. The plastic sheath 22 is preferably Teflon ® shrink tubing which is first fitted over the core wire 20 and then subjected to heat so as to cause it to shrink and fit tightly on the outer surface of the core wire 20.

Figure 2:
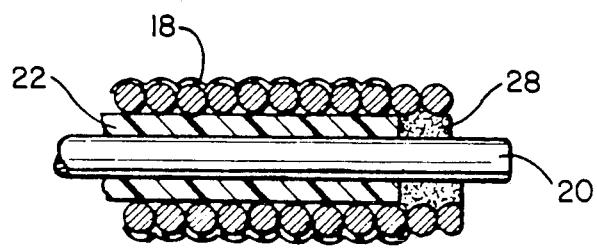
FIG. 2 is a detail of the distal end portion of the implement of FIG. 1.

With continued reference to the drawings, it is to be noted that the outer coating 18 is removed from the one or two convolutions located at the distal end 16 of the helically wound wire 12 to create an exposed electrode surface. Moreover, the core wire 20 has a distal end 24 flush with coils or projecting outward slightly beyond the distal end 16 of the helically wound wire to form a second electrode. FIG. 2 shows a detailed cross-section of the distal tip portion of FIG. 1 and shows how an insulating, high-temperature ceramic material has been plasma sprayed between the exposed tip of core wire 20 and the most distal convolution(s) of the helically wound wire 12 to provide mechanical support in the area of the electrode gap.

Connected to the proximal end 14 of the helically wound wire 12 is a terminal member 26 which is arranged to be connected to an output terminal of a RF electrosurgical generator (not shown). Likewise, the core wire 20 is connected to a separate output terminal of the electrosurgical generator, allowing a high frequency voltage to be developed across the distal end 24 of the core wire 20 and the uninsulated turns of the helically wound wire 12. Being so energized, when the distal end of the implement 10 is pressed against body tissue, a low resistance path is established between the projecting end of the core wire and the guidewire 12 allowing for the formation of an electrical arc therebetween. The concentrated heat energy of the arc permits the implement to tunnel through the tissue with which it is brought into contact.

The invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. An electrosurgical instrument for tunneling through a tissue body comprising:
   (a) a relatively thin, flexible conductive core wire of a predetermined diameter having a proximal end and a distal end;
   (b) a continuous layer of insulating material adhered to said core wire except for an exposed portion at said proximal and distal ends, said layer being sufficiently thin and pliable so as not to impair the flexibility of said core wire;
   (c) a helical coil of conductive wire of a predetermined length wrapped onto said layer of insulating material and extending over substantially the entire length thereof with adjacent convolutions of said helical coil abutting one another, said helical coil having a proximal end and a distal end and a coating of insulation on the exterior surface of said coil except for a predetermined number of convolutions at said distal end thereof, said exposed portion at said distal end of said core wire flush with or extending beyond said distal end of said coil and spaced therefrom by a predetermined gap, said gap free of electrical insulation, said coil wrapped about said core wire exhibiting a predetermined flexibility sufficient to allow same to be routed through a tortuous path within the lumen of a hollow body organ, said core wire being immovable longitudinally relative to said helical coil and the surface area of said exposed portion of said core wire being substantially less than the surface area of said predetermined number of convolutions; and
   (d) terminal means connected to said exposed portion of said proximal end portion of said core wire and to said proximal end of said coil for receiving a voltage therebetween sufficient to create a spark discharge between said exposed portion of said distal end of said core wire and said predetermined number of convolutions to effect tunneling through said tissue body.

2. The implement as in claim 1 wherein said layer of insulating material covering said core wire comprises heat shrinkable plastic.

3. The implement as in claim 1 wherein said coating of insulating material on said helical coil is a sprayed plastic material.

4. The implement as in claim 1 wherein said helical coil is stainless steel has an outer diameter in the range of from 0.025 and 0.05 inch.

5. The implement as in claim 4 wherein said core wire has an outer diameter in the range of from 0.010 to 0.020 inch.

6. The implement as in claim 1 wherein said helical coil is an intravascular guidewire.

7. The implement as in claim 1 wherein said helical coil and/or core wire is anodized aluminum, where the anodized surface acts as the insulator.

8. The implement as in claim 1 where a ceramic material is plasma sprayed into said gap between electrodes.

* * * * *